United States Patent [19]

Bogdanovic

[11] 4,454,243

[45] Jun. 12, 1984

[54] CATALYST SYSTEM FOR PRODUCTION OF ORGANOLITHIUM COMPOUNDS AND LITHIUM HYDRIDE

[75] Inventor: Borislav Bogdanovic, Mulheim, Fed. Rep. of Germany

[73] Assignee: Studiengesellschaft Kohle mbH, Mulheim, Fed. Rep. of Germany

[21] Appl. No.: 344,907

[22] Filed: Feb. 2, 1982

Related U.S. Application Data

[62] Division of Ser. No. 127,011, Mar. 4, 1980, Pat. No. 4,354,982.

[30] Foreign Application Priority Data

Mar. 7, 1979 [DE] Fed. Rep. of Germany ....... 2908928

[51] Int. Cl.³ .............................................. B01J 31/12
[52] U.S. Cl. ................................... 502/167; 502/168; 502/169
[58] Field of Search .................... 252/429 R; 502/167, 502/168, 169

[56] References Cited

U.S. PATENT DOCUMENTS 4,031,147 6/1977 Graham ........................... 252/429 R
4,075,253 2/1978 Horiie et al. ..................... 260/665 R Primary Examiner—W. J. Shine
Attorney, Agent, or Firm—Sprung, Horn, Kramer & Woods

[57] ABSTRACT

A catalytic system is provided for the lithiation of $\alpha$-olefins and $\alpha,\omega$-diolefins with concurrent production of lithium hydride. The catalysts include oxygen and sulfur containing organic compounds and polycyclic aromatics which can be combined with alkali metal and/or transition metal compounds. High yields of pure and stereospecific lithiated olefins are obtainable.

35 Claims, No Drawings

CATALYST SYSTEM FOR PRODUCTION OF ORGANOLITHIUM COMPOUNDS AND LITHIUM HYDRIDE

This is a division of application Ser. No. 127,011, filed Mar. 4, 1980, now U.S. Pat. No. 4,354,982.

FIELD OF THE INVENTION

The present invention relates to a catalyst system for the preparation of organolithium compounds from lithium and olefins with concurrent production of an equimolar amount of lithium hydride,

BACKGROUND OF THE INVENTION INCLUDING PRIOR ART

The conventional technical method of producing organolithium compounds (Kirk-Othmer, "Enc. Chem. Techn.", Vol 12, p. 547, 1967) is based on the reaction of lithium metal with organic halogen compounds, in which organolithium compounds as well as lithium halides are produced:

$$RX + 2Li \rightarrow RLi + LiX \tag{1}$$

X=Cl, Br, I

Allyllithium and benzyllithium compounds may among others be produced by the splitting of the corresponding ether derivative or acyloxy derivative with lithium metal (J. A. Katzen-ellenbogen R. S. Lenox, J. Org. Chem., 38, 326, 1973; U. Schollkopf in "Methoden der Organischen Chemie", Houben-Weyl, XIII/1, P. 161; J. J. Eisch, A. M. Jacobs, J. Org. Chem. 28, 2145 1963):

$$ROR' + 2Li \rightarrow R\text{-}Li + R'OLi \tag{2}$$

R=allyl, benzyl
R'=phenyl, mesitoyl

From the organolithium compounds so produced, numerous other organolithium compounds may be obtained by means of metal-H exchange:

$$R\text{-}Li + R'H \rightarrow R\text{---}H + R'\text{---}Li \tag{3}$$

or by means of metal-halogen exchange (D. Seebach. K.-H. Geiss in "New Applications of Organometallic Reagents in Organic Synthesis", p. 1, Elsevier, 1976):

$$R\text{-}Li + R'\text{---}X \rightarrow R'\text{---}Li + R\text{---}X \tag{4}$$

X=Cl, Br, I

Only in exceptional cases had it heretofore been possible to synthesize organolithium compounds directly from lithium metal and hydrocarbons. Thus, for instance, 1-alkines (H. Ogura, H. Takashi, Synth. Commun., 3 135, 1973), triphenylmethane or acenaphtylene (B. J. Wakefield, "The Chemistry of Organolithium Compounds", p. 70, Pergamon Press, 1974) may be lithiated with metallic lithium. According to D. L. Skinner et al (J. Org. Chem., 32, 105, 1967) lithium reacts with 1-alkenes in the absence of a solvent to produce 1-alkinyllithium compounds and lithium hydride.:

$$RCH=CH_2 + 4\ Li \rightarrow RC\equiv C\text{---}Li + 3\ LiH \tag{5}$$

whereby 1-lithio-1-alkenes are produced as byproducts of the reaction, at very small yields. In the presence of tetrahydrofuran (THF) 1-lithio-1-hexene was obtained from lithium and 1-hexene at boiling temperatures, at 9% yield.

A procedure for the preparation of organolithium compounds from lithium and ethylene in dimethoxymethane or THF in the presence of biphenyl and, if the case, naphthalene was recently made known (V. Rautenstrauch of Firmenich S.A., Geneva, Swiss Patent No. 585, 760, May 20, 1974; V. Rautenstrauch, Angew, Chem., 87, 254, 1975). The yields of organolithium compounds according to these procedures are at very low levels. Since the reaction products furthermore occur in the form of a mixture of vinyl-lithium and 1,4-dilithiobutane, this procedure hardly seems suitable for technical purposes.

SUMMARY OF THE INVENTION

The present invention provides a catalyst comprising a composition of the formula

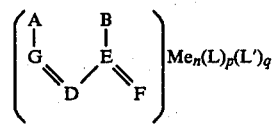

wherein
A and B are sulfur or oxygen
G is a carbon atom bonded to a radicl $R^1$
D is a carbon atom bonded to a radical $R^2$ and there is a double bond between the carbon atom of G and of D;
E is carbon
F is oxygen, sulfur,

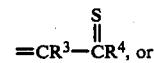

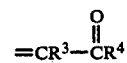

Me is an alkali metal
n is an integer from 2 to 20;
L and L' are mono or poly-functional ethers or amines;
p and q are integers from 0 to 4;
$R^1$, $R^2$, $R^3$ and $R^4$ are independently hydrogen, alkyl, cycloalkyl, aralkyl or aryl groups
and/or two or more of such groups are closed into an aliphatic or aromatic ring system; and
a metal compound of transition metals from group Ib, IIb, IVb, Vb, VIb, VIIb and VIII of the transition metals of the periodic system.

Preferably $R^1$, $R^2$, $R^3$, $R^4$ have less than about 20 carbon atoms. Alkyl groups include methyl, ethyl, isopropyl, n decyl, stearyl.

Cycloalkyl groups include cyclopentyl, cyclohexyl, decahydronaphthyl.

Aralkyl groups include benzyl, phenylethyl and naphthyl methyl. Aryl groups include phenyl, tolyl, xylyl, naphthyl, penanthryl and diphenyl.

Two groups closed in to an aliphatic ring system include propylene and butylene groups.

Two groups closed into an aromatic ring system include benzo and naphtho groups.

Preferably the ratio of moles of the composition of the formula (*) to the moles of transition compound is in the range from about 1:10 to 10:1.

In the formulas (*) above, () and (*) below, certain single bonding lines may represent double bonds and there can also be a bond between A and B when both A and B are sulfur.

Preferred catalysts of the present invention includes those wherein the composition has the following formula:

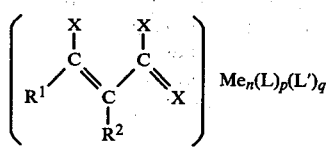

and wherein X is sulfur or oxygen.

A more preferred composition has the formula

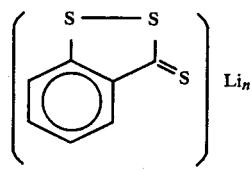

and the metal compound is cuprous chloride of ferric chloride.

Another preferred catalyst has a composition of the formula

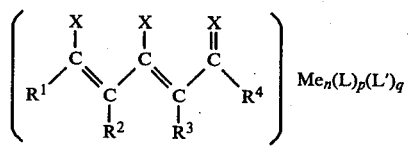

wherein X is sulfur or oxygen.

More preferred are catalysts of the formula (II) wherein X is sulfur,
$R^1 = R^4$ is $C_6H_5$, and
$R^2 = R^3$ is hydrogen and
Me is lithium and
wherein the metal compound is zinc chloride, or palladium chloride or
wherein X is sulfur
$R^1 = R^3$ is $C_6H_5$,
$R^2 = R^4$ is hydrogen and
Me is lithium, and
wherein the metal compound is cupric chloride.

The metal compound can be of a metal selected from the groups consisting of copper, gold, zinc, cadmium, titanium, zirconium, vanadium, niobium, tantalum, chromium, molybdenum, tungsten, manganese, iron, cobalt, nickel, ruthenium, rhodium, palladium, osmium, iridium and platinum.

Preferred metal compounds are of a metal selected from the group consisting of copper, iron, zinc, palladium, platinum and rhodium.

Preferred metal compounds include halides and organic complexes such as acetylacetonites, more preferred are transition metal chlorides.

Exemplary metal compounds include compounds selected from the group consisting of
zinc chloride,
iron (III) chloride
copper (I) chloride
copper (II) chloride
molybdenum (VI) chloride
titanium (IV) chloride
chromium (III) chloride
molybdenum (V) chloride
managanese (II) chloride
cobalt (II) chloride
nickel (II) chloride
nickel (II) acetylacetonate
rhodium (III) chloride
platinum (II) chloride
palladium (II) chloride The metal compound is preferably an anhydrous metal compound.

In one aspect, the present invention provides a catalyst composition of metal complexes comprising
a polycyclic aromatic compound;
an alkali metal; and
a metal compound of transition metals from group Ib, IIb, IVb, Vb, VIb, VIIb and VIIIb of the periodic system.

The polycyclic aromatic compound has preferably from about 10 to 24 carbon atom. Typical aromatic compounds include
naphthalene,
anthracene,
phenanthrene, and
diphenyl.

The alkali metal can be lithium, sodium or potassium and more preferred is lithium.

The present invention also provides a process for preparation of organo lithium compounds and lithium hydride comprising contacting lithium with a α olefin or an α,δ-diolefin in the presence of a catalyst comprising:
a metal organic composition of the formula

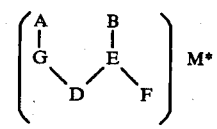

wherein
A and B are sulfur or oxygen,
G is carbon bonded to a radical $R_1$
D is carbon bonded to a radical $R_2$, and, if A and B are oxygen, also to a hydrogen atom,
E is carbon,
F is a member of the group consisting of oxygen, sulfur, hydroxy where B is oxygen,

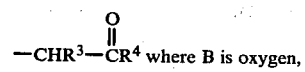

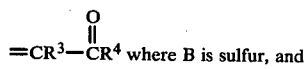

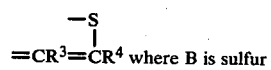

$R^1$, $R^2$, $R^3$, $R^4$ represent hydrogen, alkyl, cycloalkyl, aralkyl or aryl groups and/or two or more of such groups are closed into an aliphatic or aromatic ring system, and M* represents a metal compound of metals from groups Ib, IIb, IVb, Vb, VIb, VIIb, and VIIIb or the periodic system and/or a group $Me_n(L)_p(L')_q$ wherein Me is an alkali metal n is an integer from 2 to 20;

L and L' are monofunctional or polyfunctional ethers or amines, and p and q are integers from 0 to 4;

and/or a composition of metal complexes comprising polycyclic aromatics, an alkali metal, and a metal compound of transition metals from group Ib, IIb, IVb, Vb, VIb, VIIb and VIIIb of the periodic system.

If A and B are sulfur in formula (II) there can be a bond between A and B and when F is $$=CR^3\overset{-S}{=}CR^4$$

there is a bond between B and the sulfur atom of the $$-\overset{-S}{CR^4}$$

group.

A preferred metal organic composition employed in the process has the formula $$\left\{\begin{array}{c} X \quad X \\ | \quad \| \\ R^1-C=C \\ \quad \quad \backslash C-X \\ \quad \quad \quad | \\ \quad \quad \quad R^2 \end{array}\right\} Me_n(L)_p(L')_q \quad (I)$$

wherein X is sulfur or oxygen and more preferred are catalysts with compositions of the formula $$\left[\begin{array}{c} \text{S——S} \\ \text{⟨benzene ring⟩=S} \end{array}\right] Li_n\text{—2 CuCl}$$

and of the formula $$\left[\begin{array}{c} \text{S——S} \\ \text{⟨benzene ring⟩=S} \end{array}\right] Li_n \cdot 2 \, FeCl_3$$

The metal organic composition can have the formula $$\left\{\begin{array}{c} X \quad X \quad X \\ | \quad \| \quad \| \\ R^1-C=C=C \\ \quad \quad | \quad | \quad \backslash R^4 \\ \quad \quad R^2 \quad R^3 \end{array}\right\} Me_n(L)_p(L')_q \quad (II)$$

wherein X is sulfur or oxygen, and preferably wherein X is sulfur, $R'=R^4$ is phenyl, $R^2=R^3$ is hydrogen and Me is lithium, and wherein the metal compound is zinc chloride or palladium chloride or wherein X is sulfur $R^1=R^3$ is phenyl $R^2=R^4$ is hydrogen, and Me is lithium, and wherein the metal compound is cupric chloride.

The metal compound of the catalyst employed in the process can be the metal compound of a metal selected from the group consisting of copper, gold, zinc, cadmium, titanium, zirconium, vanadium, niobium, tantalum, chromium, molybdenum, tungsten, manganese, iron, cobalt, nickel, ruthenium, rhodium, alladium, osmium iridium and platinum, and preferably the metal compound is of a metal selected from the group consisting of copper, iron, zinc, palladium, platinum and rhodium.

Typical metal compounds include those selected from the group consisting of zinc chloride,
iron (III) chloride,
copper (I) chloride,
copper (II) chloride,
molybdenum (VI) chloride,
titanium (IV) chloride,
chromium (III) chloride,
molybdenum (V) chloride,
manganese (II) chloride,
cobalt (II) chloride,
nickel (II) chloride,
nickel (II) acetylacetonate,
rhodium (III) chloride,
platinum (II) chloride and
palladium (II) chloride.

Preferably the metal compound is an anhydrous metal compound.

A solvent can be added to the lithium, to the α-or the α,δ-diolefin and/or to the catalyst.

The solvents include cyclic or an open-chain monoether or polyethers such as the tetrahydrofuran. The catalyst can be formed in situ, by contacting lithium with compounds of the general formula III and IV, or V, VI and VII $$\begin{array}{cc} \overset{S——S}{R^1\diagdown C=C\diagdown} & \overset{O \quad OH}{\diagdown C\diagdown} \\ \overset{|}{C}-X R^1 & CH\diagdown O \\ \overset{|}{R^2} & \overset{|}{R^2} \\ \text{III} & \text{IV} \end{array}$$

$$\begin{array}{cc} \overset{S——S——S}{R^1\diagdown C=C=C\diagdown R^4} & \overset{S——S \quad O}{R^1\diagdown C=C\diagdown C\diagdown R^4} \\ \overset{|}{R^2} \overset{|}{R^3} & \overset{|}{R^2} \overset{|}{R^3} \\ \text{V} & \text{(VI)} \end{array}$$

-continued

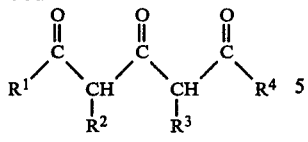

(VII)

wherein X is sulfur or oxygen and alternatively lithium is contacted with compounds of the general formula III, IV, V, VI, or VII and with a metal compound of transition metals from groups Ib, IIb, IVb, Vb, VIb, VIIb, and VIII of the periodic system.

Also lithium can be contacted with a catalyst consisting of isolated adducts between compounds III to VII, and metal compounds of transition metals from groups Ib, IIb, IVb, Vb, VIb, VIIb and VIIIb of the periodic system.

Preferably a member of the group consisting of the reaction products of the formula

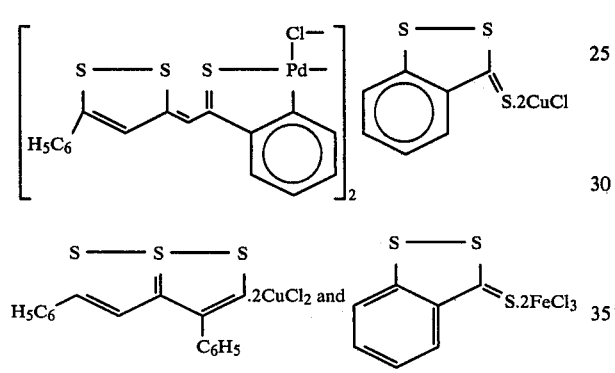

is contacted with lithium.

In a further aspect of the invention lithium is contacted with a catalyst, producted from a polycyclic aromatic compound such as anthracene, naphthalene or biphenyl and a metal compound of metals from subgroups I, II, IV, V, VI, VII and VIII of the periodic system.

The contacting can be from about $-100°$ C. to $+100°$ C., and is preferably from about $-20°$ C. and $+50°$ C. Preferably the partial pressures prevailing in the process are less than about 100 bar. The $\alpha$-olefines include those of the general formula $CH_2=CHR$, wherein R is H, alkyl, aryl, cycloalkyl or aralkyl, and the $\alpha,\omega$ diolefins include those of the formula $CH_2=CH-(CHR-)_n-CH=CH_2$ wherein R is hydrogen, alkyl, aryl, cycloalkyl or aralkyl and n is an integer from 1 to 6.

In a further aspect of the invention, a process is provided for preparation of a catalyst comprising contacting an organic compound of the formula

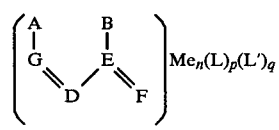

wherein
A and B are sulfur or oxygen
G is a carbon atom bonded to a radical $R_1$
D is a carbon atom bonded to a radical $R_2$ and there is a double bond between the carbon atom of G and of D.
E is carbon
F is oxygen sulfur,

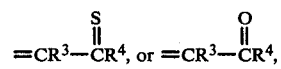

$R^1$, $R^2$, $R^3$ and $R^4$ are independently hydrogen, alkyl, cycloalkyl, aralkyl or aryl groups and/or two or more of such groups are closed into an aliphatic or aromatic ring system;
an alkali metal; and
mono or poly-functional ethers or amines.

A metal compound of transition metals from groups Ib, IIb, IVb, Vb, VIb, VIIb and VIII of the periodic system can be added to the resulting composition.

Preferred organic compounds in preparing the catalyst include those of the formulas

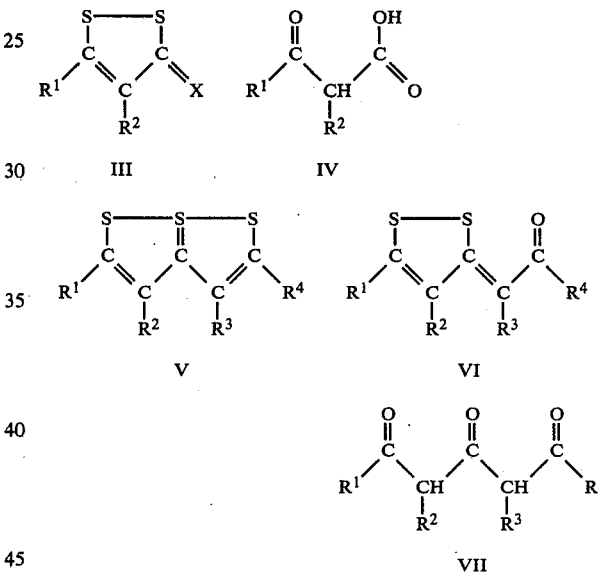

wherein X is sulfur or oxygen.

DETAILED DESCRIPTION OF THE INVENTION INCLUDING PREFERRED EMBODIMENTS

In accordance with the present invention, it was surprisingly found that $\alpha$-olefins and $\alpha\omega$-diolefins can be reacted with metallic lithium in the presence of appropriate catalysts, and the reaction products include pure and stereo epecific organolithium compounds and lithium hydride. The reaction between lithium and olefins is carried out for practical reasons in solvent such as a cyclic or open-chain monoether or polyether (preferably tetrahydrofuran, THF) at temperature from about $-100°$ to $+100°$ C. and preferably from about $-20°$ C. to $+50°$ C. and at partial pressures of preferably below 1 bar and at from about 1 to 100 bar pressure.

Accordingly, the invention relates to a process for production of organolithium compounds in addition to lithium hydride, wherein lithium is contacted with a catalyst from the following group:

(a) an alkali-metal complex compound of the general formula I or II

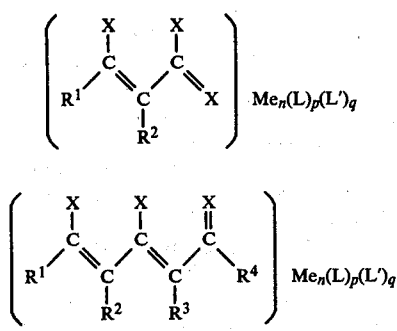

wherein
Me is an alkali metal;
X is sulfur or oxygen;
n is an integer from 2 to 20;
L and L' are monofunctional or polyfunctional ethers or amines;
p and q are integers from 0 to 4;
$R^1$, $R^2$, $R^3$ and $R^4$ are hydrogen, alkyl, cycloalkyl, aralkyl or aryl groups; and/or where two or more of such groups are closed into an aliphatic or aromatic ring system; or (b) a catalyst according to (a) in the presence of a metal compound of transition metals from group Ib, IIb, IVb, Vb, VIb, VIIb, and VIII of the periodic system; or (c) a catalyst, produced from polycyclic aromatics such as anthracene, naphthalene and biphenyl and alkali metal in the presence of a metal compound of transition metals from group Ib, IIb, IVb, Vb, VIb, VIIb, and VIII of the periodic system; or (d) adducts between compounds of the general formula III to VII

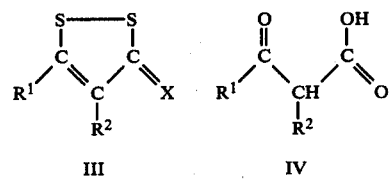

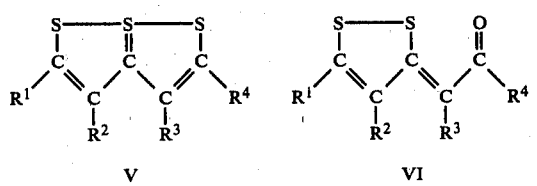

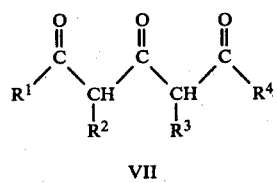

in which $R^1$, $F^2$, $R^3$ and $R^4$ have the meanings indicated under (a), and transition-metal compounds of transition metals from group Ib, IIb, IVb, Vb, VIb, VIIb and VIII of the periodic system in a solvent with an α-olefin or α,ω-diolefin.

The catalysts mentioned above under (a) and their preparation are described in German Patent Disclosure Record 27 22 221.5.

The invention furthermore relates to catalysts from
(a) an alkali metal complex compound of the general formulae I or II

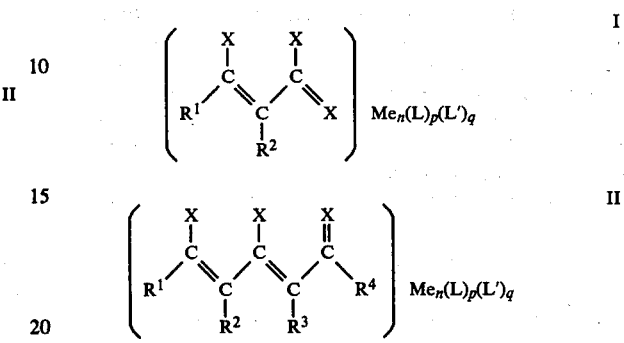

in which Me is an alkali-metal; X is sulfur or oxygen; n is an integer from 2 to 20; L and L' are monofunctional or polyfunctional ethers or amines; p and q are integers from 0 to 4; $R^1$, $R^2$, $R^3$ and $R^4$ are hydrogen, alkyl, cycloalkyl, aralkyl or aryl groups and/or where two or more of such groups are closed into an aliphatic or aromatic ring system; and (b) metal compounds of transition metals from group Ib, IIb, IVb, Vb, VIb, VIIb, and VIIIb of the period system or from (c) complexes of polycyclic aromatics such as anthracene, naphthalene and biphenyl, and an alkali-metal with (d) a metal compound of transition metals of group 1B, IIb, IVb, Vb, VIb, VIIb, and VIIIb of the periodic system.

Among the metals from the group Ib, IIb, IVb, Vb, VIb, VIIb and VIIIb of the periodic system are included copper, gold, zinc, cadmium, titanium, zirconium vanadium, niobium, tantalum, chromium, molybdenum, tungsten, manganese, iron, cobalt, nickel, ruthenium, rhodium, palladium osmium, iridium or platinum. Of these, we prefer copper, iron, zinc, palladium, platinum and rhodium.

Examples for the monofunctional or polyfunctional ethers or amines designated by an L or L', in general formulae I and II, are as follows: Cyclic ethers such as tetrahydrofuran or glycol ether, and amines such as tetramethylethylene diamine or morpholine. The monofunctional or polyfunctional ethers or amines have preferably less than about 10 carbon atom. Catalyst formation may also be carried out in a manner such that compounds of the general formula III, IV, V, VI, and VII—which are also described in German Patent Disclosure Record No. 27 22 221.5—are mixed with alkali metals, preferably lithium, and, if appropriate, with a metal compound of metals from subgroups I, II, IV, V, VI, VII and VIII of the periodic system, in an appropriate solvent; and, if appropriate, in the presence of α-olefins or α,ω-diolefins. A particularly active and selectively operating catalyst system, in the sense of the present procedure, is produced, if 2,5-diphenyl-1,6,6a-trithiapentalene (V, $R^1=R^4=C_6H_5$, $R^2=R^3=H$) is converted in combination with zinc chloride in the presence of α-olefins or α,ω-diolefins in THF with lithium (see Examples 40–42).

Finally, it is also possible to let isolatable adducts between compounds of the general formulae III-VII, listed above under (d), and transition-metal compounds of subgroups I, II, IV, V, VI, VII or VIII of the periodic system operate as catalysts on the lithium and olefin or diolefin. Thus, for instance, iron (III) chloride, copper (I) chloride, and copper (II) chloride, as well as molybdenum (V) chloride form, with 1,2-dithiol-3-thiones or 1,6,6a-trithiapentalenes, 2:1 adducts which may be used instead of a mixture of both components to produce the catalysts. By the same token, the complex ortho-chloropalladio-2,5-diphenyl-1,6,6a-trithiapentalene (6) which can be produced from 2,5-diphenyl-1,6,6a-trithiapentalene and PdCl₂ yields with lithium in THF an active catalyst for the lithiation of olefins:

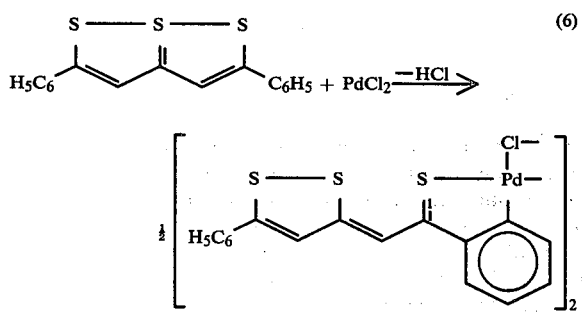

The catalytic lithiation of ethylene with the aid of the catalysts according to the invention, in for instance THF, lead to vinyllithium and lithium hydride:

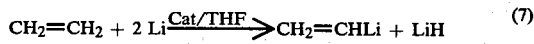

The vinyllithium soluble in THF may be separated from the insoluble lithium hydride and may be further used in solution or isolated in crystalline form. Depending on the catalyst, the yields of vinyllithium range from 60 to more than 70% of the amount calculated according to (7).

In the catalytic lithiation of propene according to the procedure of the invention, there are generally produced four isomeric organolithium compounds: Trans-1-propenyllithium (9), cis-1-propenyllithium (10), isopropenyllithium (11) and allyllithium (12), in addition to lithium hydride:

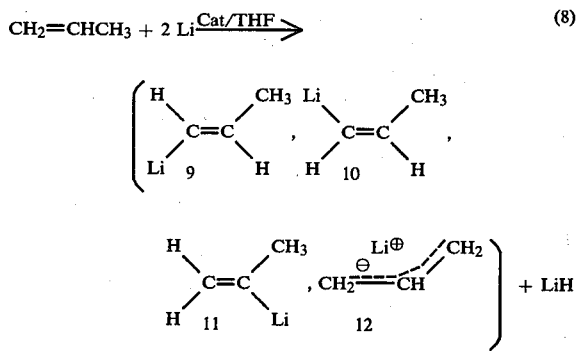

The selectivity of this reaction in relation to the formation of individual isomers may be controlled through the selection of the catalysts. Thus, in the presence of catalysts produced with the use of iron, copper, cobalt or zinc compounds, trans-1-propenyllithium 9 is produced at high selectivity. On the other hand, the catalytic lithiation of propene may be controlled by using palladium, platinum or rhodium compounds in a manner such that predominantly allyllithium 12 is produced. One catalyst that operates in a particularly selective fashion in this sense was found to be the palladium complex (6), with the aid of which allyllithium may be obtained with a selectivity of 85-90%. In the example of lithiation of 1-butene with this palladium complex as a catalyst it is shown that higher α-olefins may also be selectively lithiated in the allyl position. On the other hand, using catalysts produced with the utilization of zinc, iron or copper compounds, higher 1 alkenes such as 1-butene, 1-pentene, 1-octene and 1,7-octadiene may also be selectively lithiated in the trans-1 position. Thus, for instance, 1-octene may be lithiated with the aid of above-mentioned catalyst from 2,5-dipheyl-1,6,6a-trithiapentalene and ZnCl₂, with a selectivity of more than 96% in the 1-trans position.

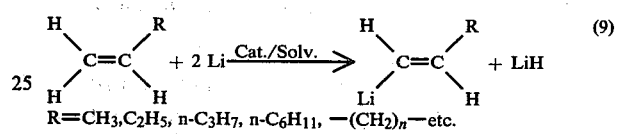

If appropriate, the trans-1-lithio-1-alkenes may be isolated in analytically pure crystalline form. By means of crystallization, the ratio of trans-1-lithio-1-alkene is generally raised. The present procedure thus permits a selective preparation of trans-1-alkenyl or allyllithium compounds from α-olefins or diolefins and lithium.

In the catalytic lithiation of 1,4-pentadiene in the presence of the 4,5-benzodithiol-3-thione.2CuCl₂ complex there is produced a heretofore unknown organolithium compound with the following structure:

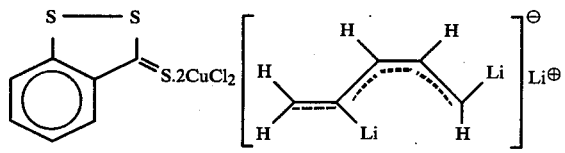

The starting point materials for the preparation of organolithium compounds in accordance with the present invention are preferably α-olefins and α,ω olefins having up to about 40 carbon atoms. They include those of the general formulae CH₂=CHR, in which R=H, alkyl, aryl, cycloalkyl or aralkyl; or diolefins of the general formula CH₂=CH—(CHR)ₙ—CH=CH₂, in which R has the same significance as above, and n=1-6.

The catalytic lithiation of α-olefins or α,ω-diolefins in accordance with the invention represents a new method of preparation of organolithium compounds which cannot be produced in any other way or can only be produced with great difficulty. In lieu of the expensive and often toxic as well as hard-to-procure organohalogen compounds, the present procedure uses commercially available olefins. Moreover, when the conventional method is used, one-half of the lithium that is used winds up as a lithium halide, and is thus lost for further conversion. The procedure according to the invention supplies, besides the organolithium compound, highly reactive and technically valuable lithium hydride. The entire amount of lithium applied is converted into valuable lithium compounds.

The present procedure permits a regioselective or stereoselective synthesis of organolithium compounds, providing the capability of controlling the reaction by the proper choice of the catalyst or the reaction conditions, in a manner such that, depending on the need, different organolithium compounds may be obtained from the same starting-point olefin.

The organolithium compounds that can be prepared by the present procedure may be used as initiators for anionic polymerisations of mono- olefins or diolefins, or as reagents for the introduction of organic unsaturated groups, as well as for reduction in organic synthesis.

The following examples represent preferred embodiments of the present invention.

EXAMPLES

All experiments for the preparation of organolithium compounds are carried out in a protective gas atmosphere, such as argon.

EXAMPLE 1

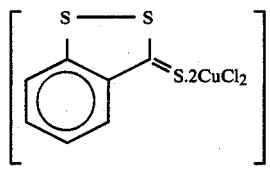
(13)

For the preparation of the 4,5-benzo-1,2-dithiol-3-thione 2CuCl$_2$-complex (13), 2.83 g (21.05 mMoles) of anhydrous copper(II) chloride are suspended in 100 ml of benzene, are added to 2.00 g (10.85 mMoles) of 4,5-benzo-1,2-dithiol-3-thione, and the mixture is stirred for 18 hours at room temperature. The suspension is filtered, the precipitate is washed with benzene and dried at $10^{-3}$ Torr. This yields 3.58 g (75% of theoretical) of the complex 13.C$_7$H$_4$S$_3$Cu$_2$Cl$_4$ (453.16); Calc. C 18.55, H 0.89, S 21.22, Cu 28.04 Cl 31.29; Found C 17.50, H 1.00, S 20.90, Cu 27.60, Cl 32.70.

A solution of 1.40 g (3.09 mMoles) of complex 13 in 100 ml of absolute THF is saturated with propene (1 bar) aat 0° C.; immediately thereafter, 5.07 g (0.73 Moles) of lithium sand is added to the solution in a propene atmosphere at 0° C., and under stirring (molar ratio 13:Li=1:236). After a temporary temperature rise, the absorption of propene starts after 10–15 minutes; the rate of propene absorption can be measured with the aid of a gas burette connected to the reaction vessel. During the propene absorption, the suspension is stirred, with propene pressure kept at 1.1–1.2 bar and temperature kept at 0° C. to +2° C. The dark brown reaction mixture absorbs 6.0 liters of propene (1 bar, 20° C.) until it is saturated within 49 hours (68.5% of theoretical). The suspension is filtered at 0° C., the precipitate is washed with THF and dried at 0.2 Torr. This yields 4.41 g of lithium hydride mixed with a little lithium (0.135 g of the mixture yield with D$_2$O 257 ml of gas (1 bar, 20° C.), consisting of HD (70%), D$_2$ (19%) and H$_2$ (11%). For the purpose of analyzing the organolithium compound in the solution, an aliquot of the solution (8.0 ml of a total of 142.0 ml) is concentrated under vacuum (0.2 torr) and the solid residue is hydrolyzed. The amount of gas produced thereby is 335.5 ml (1 bar, 20° C.) and consists of propene (84.9%), THF (4.6%), H$_2$ (3.5% and acetylene (1.4%). From the amount of propene, Equ.8 permits calculation of a yield in organolithium compounds LiC$_3$H$_5$ of 57.7%. In order to determine the distribution of isomers, 58.0 ml of the solution are concentrated under vacuum (0.2 torr), the residue is dissolved in 60 ml of ether, mixed at 0° C. with 18.9 g (174 mMoles) of trimethylchlorosilane, and the mixture is stirred 12 hours at 20° C. Hydrolysis or processing and distillation produces, in addition to hexamethyldisiloxane, 7.3 g of a mixture of the isomeric silanes (CH$_3$)$_3$SiC$_3$H$_5$ (B.P. 87°-89° C./760 torr), consisting of trans-1-propenyltrimethylsilane 74.5%, cis-1-propenyltrimethylsilane 1.7%, isopropenyltrimethylsilane 8.1%; and allyltrimethylsilane 15.3%.

In order to isolate the trans-1-propenyllithium (9), 74.0 ml of the solution are concentrated under vacuum (0.2 torr) to 33.0 ml, added to 50 ml pentane, mixed for 10 minutes and filtered. For the purpose of crystalizing (9) the filtrate is kept for 3 hours at −40° C. and for 12 hours at −78° C. The crystals of (9) are filtered at −78° C., was washed three times with 40 ml of cold pentane each, dried for one-half hour at −30° C., one-half hour at 0° C. and one hour at 20° C. under vacuum (0.2 torr). This yields 9.25 g of the trans-1-propenyllithiumtetrahydrofuran adduct, in the form of light brown crystals (Li-content 6.51; yields 45.6% of theoretical, referred to lithium). The $^1$H-NMR spectrum of the product

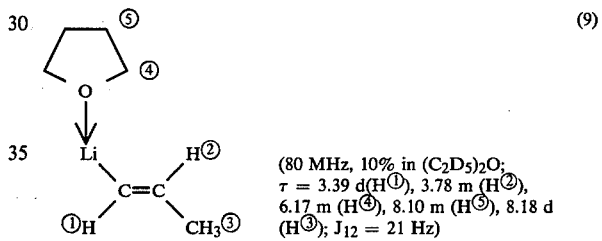

(9)

(80 MHz, 10% in (C$_2$D$_5$)$_2$O; $\tau$ = 3.39 d(H①), 3.78 m (H②), 6.17 m (H④), 8.10 m (H⑤), 8.18 d (H③); J$_{12}$ = 21 Hz)

agree with that of D. Seyferth and L. G. Vaughan (J. Organomet. Chem. 1, 201, 1963) prepared from trans-1-chloro-1-propene and lithium (9).

For further purification, 9.0 g of the raw material are recrystalized from a mixture of 18 ml of THF and 32 ml of pentane, as described above. This yields 6.5 g trans-1-propenyllithiumtetrahydrofuran adduct, in the form of colorless crystals. C$_3$H$_5$Li.C$_4$H$_8$O (M.W.=120.0); calc. 5.78% Li; found 5.75 Li. The conversion of 6.0 g (49.7 mMole) of this product with trimethylchlorosilane, as described above, yields 5.43 g of (CH$_3$)$_3$SiC$_3$H$_5$ with the following composition: trans-1-propenyltrimethylsilane, 93.4%; cis-1-propenyltrimethylsilane, 0.4%; isopropenyltrimethylsilane, 1.3%; and allyltrimethylsilane, 4.9%.

EXAMPLE 2

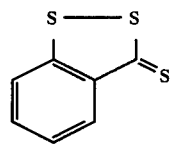
(3a)

A solution of 0.90 g (4.9 mMole) of 4.5-benzo-1,2-dithiol-3-thione (BDT) (3a) and 1.63 g (9.8 mMoles) of FeCl$_3$ in 100 ml of THF are saturated with propene (1 bar) at 0° C.; immediately afterwards 4.87 g (0.70

Moles) of lithium sand are added to the solution in propene atmosphere at 0° C. and with mixing (molar ratio 3a:FeCl$_3$:Li=1:2:143). After a temporary temperature rise, the propene absorption starts after 10-15 minutes. During the propene absorption, the suspension is stirred, the propene pressure is kept at 1.1-1.2 bar and the temperature is kept at 0° C. to +2° C. The reaction mixture absorbs until saturation within 71 hours, 3.8 liters of propene (1 bar, 20° C.). The suspension is filtered and the lithium hydride is washed with THF. Of the total of 114.0 ml of the filtrates, 8.0 ml are hydrolyzed as described in example 1 whereby 351 ml of gas (1 bar, 20° C.) with the composition propene, 75.7%; THF, 7.8%, H$_2$, 8.7%, and acetylene 2.7% are released. From the amount of propene, a total yield of LiC$_3$H$_5$ of 45% is calculated according to Equ. 8. In the silylation of an aliquot of filtrate, as described in example 1, one obtains a mixture of isomeric silanes (CH$_3$)$_3$SiC$_3$H$_5$, of the following composition: trans-1-propenyltrimethylsilane, 83.8%; cis-1-propenyltrimethylsilane, 1.3%; isopropenyltrimethylsilane, 10.3%; and allyltrimethylsilane, 4.6%. This result means that in the present case the catalytic lithiation of propene occurs with a selectivity of 83.8% in the trans-1-position of the propene.

EXAMPLES 3 to 12

For the preparation of the 2,4-diphenyl-1,6,6a-trithiapentalene 2CuCl$_2$-complex (15) Example 6, 3.09 g (23.0 mMoles) of anhydrous copper(II)chloride are suspended in 100 ml of toluene, added to

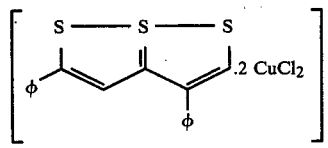

3.73 g (12.0 mMoles) of 2,4-diphenyl-1,6,6a-trithiapentalene, and the mixture is stirred for 18 hours at room temperature. The suspension is filtered, the precipitate is washed with toluene, and dried at 10$^{-3}$ torr. One obtains 4.0 g (60% of theoretical) of the complex (15). C$_{17}$H$_{12}$S$_3$Cu$_2$Cl$_4$ (580.8). calc. C 35.12, H 2.07, S 16.56, Cu 21.88, Cl 24.41. Found C 34.85, H 2.55, S 16.34, Cu 21.78, Cl 24.35.

Implementation of the examples 3 to 12 (Table 1): the components of the catalysts are previously added to THF, the suspension is stirred if appropriate for 12 hours at 20° C.; immediately thereafter, the preparations are saturated at respective reaction temperature with propene (1 bar), and lithium sand is added in a propene atmosphere under stirring. The amounts of propene absorbed after specific reaction times (in liters, at 1 bar, 20° C.), as well as the yields of LiC$_3$H$_5$ and the isomer ratios (9:10:11:12) are indicated in Table 1. The determination of the yields and the isomer ratios are carried out as described in Example 1.

TABLE 1

| | | | | | | Propene | | | | | |
|---|---|---|---|---|---|---|---|---|---|---|---|
| | | | | | Rct. | Rct. | Ab- | LiC$_3$H$_5$ | Composition of LiC$_3$H$_5$ | | |
| Example | Catalyst | | THF | LiSand | Temp | Time | sorption | Yield | (9) | (10) (11) | (12)$^{(a)}$ |
| No. | g (mMoles) | | (ml) | g (Mole) | (°C.) | (Hrs) | (liters) | [%] | | % | |
| 3 | (13) 1.31 (2.9) | | 70 | 1.90 (0.27) | 0 | 74 | 2.54 | 75 | 62.4 | 1.8  14.9 | 20.9 |
| 4 | 0.39 (2.1) + 2CuCl$_2$$^{(b)}$ 0.57 (4.2) | | 50 | 1.30 (0.19) | −20 | 48 | 1.08 | 31 | 76.6 | 1.1  12.6 | 9.7 |
| 5 | 0.53 (1.7) + 2CuCl$_2$$^{(b)}$ 0.46 (3.4) | | 70 | 1.60 (0.23) | 0 | 52 | 2.31 | 78 | 52.1 | 1.0  9.0 | 37.2 |
| 6 | (15) 1.01 (1.74) | | 50 | 1.06 (0.15) | +20 | 48 | 0.79 | 43 | 58.2 | 1.1  0.4 | 40.2 |

TABLE 1-continued

Catalytic Reaction of Lithium with $C_3H_6$ to $LiC_3H_5$ and LiH

| Example No. | Catalyst g (mMoles) | THF (ml) | LiSand g (Mole) | Rct. Temp (°C.) | Rct. Time (Hrs) | Propene Absorption (liters) | $LiC_3H_5$ Yield [%] | Composition of $LiC_3H_5$ (9) | (10) | (11) | (12)$^{(a)}$ % |
|---|---|---|---|---|---|---|---|---|---|---|---|
| 7 | 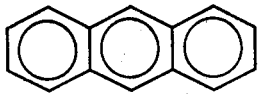 + 2CuCl$_2$$^{(b)}$  0.27 (1.5)  0.42 (3.1) | 50 | 1.42 (0.20) | 0 | 42 | 1.22 | 45 | 78.0 | 1.9 | 13.0 | 7.0 |
| 8 | 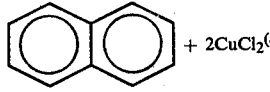 + 2CuCl$_2$$^{(c)}$  0.65 (5.1)  1.34 (10.0) | 150 | 4.80 (0.69) | 0 | 120 | $(d)$ | 41 | 79.2 | 1.6 | 8.9 | 10.3 |
| 9 | φ—φ + 2CuCl$_2$$^{(c)}$  0.83 (5.4)  1.46 (10.8) | 100 | 5.67 (0.82) | 0 | 67 | 2.58$^{(d)}$ | 38 | | | | |
| 10 | 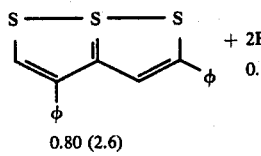 + 2FeCl$_3$$^{(b)}$  0.84 (5.2)  0.80 (2.6) | 70 | 1.70 (0.24) | 0 | 48 | 1.71 | 47 | 82.3 | 1.9 | 9.4 | 6.5 |
| 11 | 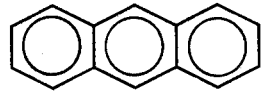 + 2FeCl$_3$$^{(c)}$  1.90 (11.7)  1.05 (5.9) | 100 | 3.96 (0.57) | 0 | 120 | 2.73$^{(d)}$ | 26 | 82.5 | 1.7 | 9.7 | 6.2 |
| 12 | 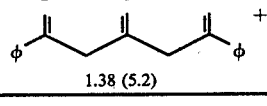 + 2FeCl$_3$  1.68 (10.4)  1.38 (5.2) | 100 | 5.27 (0.76) | 0 | 98 | 2.78$^{(d)}$ | 22 | 85.5 | 2.0 | 10.2 | 2.3 |

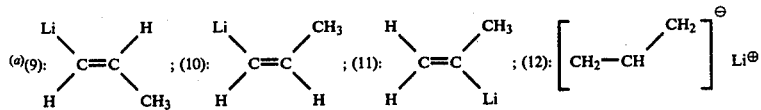

$^{(b)}$Before addition of Li, the sample was stirred for 12 hours at 20° C.
$^{(c)}$The respective aromatic compound and metal salt were previously added to THF, the solution was saturated with $C_3H_6$, and Li was added.
$^{(d)}$A propene pressure of 1.1–1.2 bar was used.

EXAMPLES 13 to 24

Implementation of Examples 13 to 24 (Table 2):
4,5-Benzo-1,2-dithiol-3-thione (BDT) (3a) and respective metal salt (molar ratio BDT:metal salt=1:2) are stirred in 60 ml of THF for 12 hours at 20° C.; immediately afterwards, the preparation is saturated at 0° C. with propene (1 bar), and lithium sand is added in a propene atmosphere and under stirring. The amounts of propene absorbed after specific reaction times (in liters, at 1 bar, 20° C.), as well as the yields of $LiC_3H_5$ and the isomer ratios (9:10:11:12) are indicated in Table 2. The determination of the yields and the isomer ratios are carried out as described in Example 1.

EXAMPLES 25 to 27

Preparation of the ortho-chloropalladio-2,5-diphenyl-1,6,6a-trithiapentalene complex (8) (Example 25):

To the suspension of 3.10 g (9.94 mMole) of 2,5-diphenyl-1,6,6a-trithiapentalene in a mixture of 230 ml of methanol and 25 ml of benzene, one adds 1.76 g (9.92 mMoles) of PdCl$_2$ followed by 1.33 g (31.3 mMoles) of LiCl dissolved in 20 ml methanol. The suspension is boiled for 3 hours under stirring, with reflux, and after cooling to room temperature it is filtered through a G-3 glass filter crucible. In the mother liquor, 93.6% of the split-off HCl was determined acidimetrically. The precipitate was washed with methanol and ether and was dried at $10^{-3}$ torr. The yield of (8) (M.P. 304° C., decomp.) amounts to 4.38 g (97%).

$C_{17}H_{11}S_3PdCl$ (453.8); Calc. C. 44.94, H 2.64, S 21.15, Pd 23.44, Cl 7.82; Fd. C 44.92, H 2.90, S 21.08, Pd 23.21, Cl 7.86.

Implementation of Examples 25 to 27 (Table 3):

TABLE 2

Catalytic Reaction of Lithium with $C_3H_6$ to $LiC_3H_5$ and LiH (At 0° C. and 1 bar of propene in 60 ml of THF. Molar ratio. 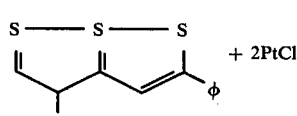 (BDT):$MeX_n$ = 1:2)

| Example No. | Catalyst g (mMoles) | LiSand g. (Mole) | Rct. Time (hrs) | Propene Absorption (liters) | $LiC_3H_5$ Yield (%) | Composition of $LiC_3H_5$ [%] | | | |
|---|---|---|---|---|---|---|---|---|---|
| | | | | | | (9) | (10) | (11) | (12)$^a$ |
| 13 | BDT + 2TiCl$_4$ 0.33(1.8)0.68(3.6) | 1.14(0.16) | 46 | 1.00 | 29 | 84.8 | 2.0 | 6.5 | 6.7 |
| 14 | BDT + 2CrCl$_3$ 0.31(1.7)0.56(3.5) | 1.20(0.17) | 46 | 1.10 | 42 | 83.1 | 1.9 | 5.5 | 9.4 |
| 15 | BDT + 2MoCl$_5$ 0.33(1.8)0.99(3.6) | 1.08(0.16) | 53 | 0.78 | 31 | 68.0 | 1.6 | 20.0 | 10.4 |
| 16 | BDT + 2MnCl$_2$ 0.44(2.4)0.60(4.8) | 1.33(0.19) | 45 | 1.38 | 37 | 75.7 | 2.4 | 7.0 | 15.0 |
| 17 | BDT + 2CoCl$_2$ 0.37(2.0)0.53(4.1) | 1.07(0.15) | 29 | 1.33 | 52 | 80.7 | 2.0 | 8.2 | 9.1 |
| 18 | BDT + 2NiCl$_2$ 0.32(1.7)0.44(3.4) | 1.30(0.19) | 72 | 1.22 | 40 | 64.8 | 1.7 | 2.4 | 31.1 |
| 19 | BDT + 2Niacac$_2^b$ 0.29(1.6)0.80(3.2) | 0.99(0.14) | 30 | 0.63 | | 67.0 | 2.3 | 2.3 | 28.4 |
| 20 | BDT + 2ZnCl$_2$ 0.41(2.2)0.61(4.5) | 1.68(0.24) | 48 | 1.60 | 53 | 83.1 | 1.0 | 9.9 | 6.0 |
| 21 | BDT + 2RhCl$_3$ 0.22(1.2)0.49(2.3) | 0.76(0.11) | 48 | 0.43 | 39 | 20.9 | 1.2 | 6.7 | 71.2 |
| 22 | BDT + 2PtCl$_2$ 0.27(1.5)0.77(2.9) | 1.05(0.15) | 48 | 1.00 | 51 | 28.0 | 0.3 | 3.4 | 68.2 |
| 23 | 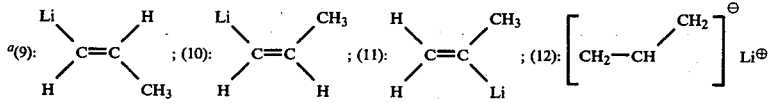 + 2PtCl$_2$ 0.29(0.9)0.49(1.8) | 0.88(0.13) | 29 | 1.01 | 66 | 39.6 | 0.6 | 5.9 | 53.8 |
| 24 | BDT + 2PdCl$_2$ 0.30(1.6)0.57(3.2) | 1.10(0.16) | 72 | 1.00 | 54 | 55.8 | 1.0 | 7.6 | 35.6 |

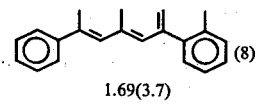

$^b$Niacae$_2$ = Nickel acetylacetonate

The solution or suspension of the catalyst in THF is saturated at 0° C. with propene (1 bar) and immediately thereafter lithium sand is added in a propene atmosphere and under stirring. The amounts of propene absorbed at the specific times (in liters, at 1 bar, 20° C.), as well as the yields of $LiC_3H_5$ and the isomer ratios (9:10:11:12) are indicated in Table 3. The determination of the yields and of the isomer ratios was carried out as described in Example 1.

TABLE 3

Catalytic Reaction of Lithium with Propene to $LiC_3H_5$ and LiH (at 0° C.)

| Example No. | Catalyst g (mMoles) | Solvent (ml) | LiSand g (Mole) | Rct. Time (hrs) | Propene Absorption (liters) | $LiC_3H_5$ Yield (%) | Composition of $LiC_3H_5$ [%] | | | |
|---|---|---|---|---|---|---|---|---|---|---|
| | | | | | | | (9) | (10) | (11) | (12)$^{(a)}$ |
| 25 | 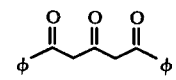 1.69(3.7) | THF (50) | 2.45(0.35) | 95 | 2.58 | 59 | 10.2 | 0.2 | 0.6 | 99.1 |
| 26 | BDT$^{(b)}$ 0.58(3.2) | THF (100) | 5.09(0.73) | | 2.48$^{(c)}$ | 22 | 77.4 | 1.7 | 13.0 | 8.0 |
| 27 |  | THF (50) | 1.53(0.22) | | 1.30 | 36 | | | | |

TABLE 3-continued

| | | Catalytic Reaction of Lithium with Propene to LiC₃H₅ and LiH (at 0° C.) | | | | | | | | |
|---|---|---|---|---|---|---|---|---|---|---|
| Example No. | Catalyst g (mMoles) | Solvent (ml) | LiSand g (Mole) | Rct. Time (hrs) | Propene Absorption (liters) | LiC₃H₅ Yield (%) | Composition of LiC₃H₅ [%] | | | |
| | | | | | | | (9) | (10) | (11) | (12)[(a)] |
| | 1.89(7.2) | | | | | | | | | |

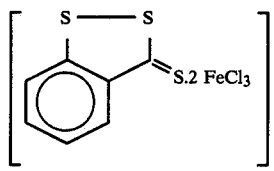

[(b)]BDT = 4,5-Benzo-1,2-dithiol-3-thione
[(c)]A propene pressure of 1.1–1.2 bar was used.

EXAMPLES 28 to 33

$$\left[ \begin{array}{c} S \text{——} S \\ \text{[benzene ring]} \end{array} \right. \left. \begin{array}{c} \\ \text{=}S.2\,FeCl_3 \end{array} \right] \quad (16)$$

Preparation of 4,5-benzo-1,2-dithiol-3thione.2 FeCl₃-complex (16) (Example 29):

To the suspension of 1.89 g (11.6 mMoles) of the anhydrous FeCl₃ in 80 ml of benzene, the solution of 1.07 g (5.8 mMoles) of 4,5-benzo-1,2-dithiol-3-thione (3a) in 70 ml of benzene is added in dropwise fashion with stirring; immediately thereafter, the mixture is stirred for 24 hours at 20° C. The suspension is filtered, the precipitate is washed with benzene and dried at $10^{-3}$ torr. One obtains 2.36 g (80% of theoretical) of the complex (16). C₇H₄S₃Fe₂Cl₆ (508.7); calc. C. 16.52, H 0.78, Fe 21.97, S 18.90, Cl 41.84; fd. C 16.55, H 082, Fe 21.91, S 18.84, Cl 41.76.

Implementation of Examples 28 to 33 (Table 4):

The catalysts are previously added to THF, the solution is saturated with ethylene (1 bar) at 0° C.; immediately thereafter, lithium sand is added at 0° C. under stirring, in an ethylene atmosphere. The amounts of ethylene absorbed after specific reaction times (in liters, 1 bar and 20° C.) are indicated in Table 4. The suspensions were filtered and the lithium hydride was washed with THF. In order to determine the yield of vinyllithium in the filtrate, aliquots of the filtrate were concentrated under vacuum and the residues were hydrolyzed. From the amounts of ethylene developed and on the basis of Equ. 7, the yields of vinyllithium indicated in Table 4 were calculated.

In order to isolate the vinyllithium, in Example 28, 85 ml of a total of 90 ml of the filtrate were concentrated under vacuum (0.2 torr), the residue was stirred with 50 ml of pentane for 30 minutes, the suspension was filtered and the solid was washed four times with 10 ml of pentane each. Upon cooling the filtrate to $-40°$ C., the vinyllithium-tetrahydrofuran adduct crysalized (2.72 g) in the form of colorless crystals.

C₆H₁₁OLi (106.1);
calc. 6.60% Li;
fd. 6.60% Li.

In order to determine the lithium hydride, in Example 32, the lithium hydride obtained upon filtration was dried at 0.2 torr, yielding 4.1 g of a gray powder with 46.7% Li. Of this powder, 0.158 g yielded upon hydrolysis the following: HD 75.0%; D₂ 6.3%; H₂ 6.3%; C₂H₃D 2.1%; and THF 1.3%. From the amount of HD, a yield of LiH of 69% was calculated according to Equ. 7.

TABLE 4

Catalytic Reaction of Lithium with Ethylene to Vinyllithium and Lithium hydride (at 0° C.)

| Example No. | Catalyst g (mMoles) | Solvent (ml) | LiSand g (Mole) | Rct. Time (hrs) | Ethylene Absorption (liters) | LiC₂H₃- Yield (%) |
|---|---|---|---|---|---|---|
| 28 | [S—S / benzene / =S.2 CuCl₃] (13) 1.07(2.4) | THF (70) | 1.70(0.24) | 44 | 2.42 | 60 |
| 29 | [S—S / benzene / =S.2 FeCl₃] (16) 0.54(1.1) | THF (50) | 0.55(0.08) | 24 | 0.68 | 72 |

TABLE 4-continued
Catalytic Reaction of Lithium with Ethylene to Vinyllithium and Lithium hydride (at 0° C.)

| Example No. | Catalyst g (mMoles) | Solvent (ml) | LiSand g (Mole) | Rct. Time (hrs) | Ethylene Absorption (liters) | LiC₂H₃- Yield (%) |
|---|---|---|---|---|---|---|
| 30 | 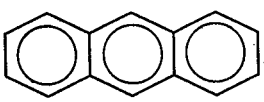 + 2 FeCl₃[a] <br> 2.1(1.2) 3.9(2.4) | THF (50) | 0.82(0.12) | 70 | 0.93 | 64 |
| 31 | 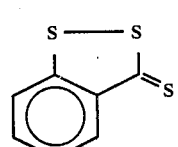 <br> 0.90(4.9) | THF (50) | 1.91(0.28) | 143 | 2.03[b] | 35 |
| 32 | 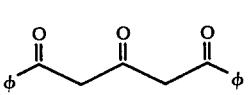 <br> 1.13(4.3) | THF (100) | 3.62(0.52) | 130 | 5.00[b] | 44 |
| 33 | 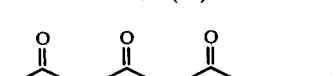 + 2 FeCl₃ <br> 0.96(3.6) 1.1(6.8) | 1,2-dimethoxy-ethane (100) | 1.94(0.28) | 67 | 0.83[b] | |

[a]Before the addition of Li, the sample was stirred for 12 hours at 20° C.
[b]An ethylene pressure of 1.1–1.3 bar was used.

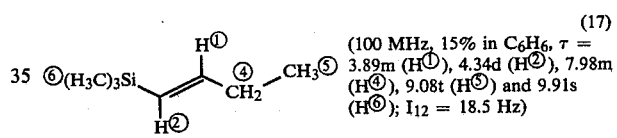

(17) (100 MHz, 15% in C₆H₆, τ = 3.89m (H①), 4.34d (H②), 7.98m (H④), 9.08t (H⑤) and 9.91s (H⑥); J₁₂ = 18.5 Hz)

EXAMPLE 34

In 100 ml of absolute THF, the following are consecutively dissolved: 0.78 g (4.2 mMoles) of 4,5-benzo-1,2-dithiol-3-thione (3a); 1.38 g (8.5 mMoles) of anhydrous FeCl₃; and, at 0° C. 24.2 g (0.43 Moles) of 1-butene; immediately thereafter, the solution was mixed at 0° C. and under stirring, with 7.30 g (1.05 Mole) of lithium sand. The reaction mixture was stirred a total of 7 days at 0° C. During this period, 5.0-ml samples of the solution were withdrawn, filtered, and their lithium content was determined acidimetrically. After 17 and 70 hours of reaction time, the samples were found to contain 6.75 and 10.6 g-atoms of lithium, corresponding to a lithium conversion to lithium butenyl and lithium hydride, according to Equ. 9, of 26 and 40%. After 7 days of reaction time, the reaction mixture was separated by filtration from the lithium hydride and the unconverted lithium, and the precipitate was washed with THF. A 4.5-ml sample of the filtrate (of a total of 138 ml) yielded upon hydrolysis 218 ml of gas (at 20° C., 1 bar), with 62.5% vol. of butene-1. From this, a yield of LiC₄H₇ of 40% was calculated according to Equ. 9.

In order to characterize the lithium butenyl, the remaining amount was mixed with an excess of trimethylchlorosilane in ether, as described in Example 1. This yields 26.2 g of a mixture of the four isomeric compounds (CH₃)₃SiC₄H₇ (B.P. 95°–109° C./760 torr), of which the main component is represented at 87.9%, according to the gas chromatogram. According to the ¹H-NMR-spectrum, the major component is trans-1-trimethylsilyl-1-butene (17), which means that the lithiation occurs with a selectivity of 87.9% in the 1-trans position of 1-butene.

EXAMPLE 35

In a manner analogous to that of Example 34, 41.4 g (0.74 Mole) of 1-butene are allowed to react in the presence of 2.15 g (4.75 mMoles) of complex (13) (Example 1) as catalyst, with 5.60 g (0.81 Mole) of lithium sand in 150 ml of THF for 10 days at 0° C. The mixture is filtered and the solid (LiH+Li) is washed with THF. Of the filtrate (totalling 186 ml), 5.0 ml yield, after evaporation of the THF and subsequent hydrolysis, 191 ml of gas (at 20° C., 1 bar), with 80% 1-butene (balance: THF, H₂ and C₂H₂). On that basis, and following Equ. 9, one calculates a yield of LiC₄H₇ of 58% (referred to Li). In order to isolate the trans-1-lithio-1-butene, 110 ml of THF is distilled off from the remaining filtrate under vacuum (0.2 torr), 100 ml of pentane are added, and the mixture is filtered [free of] catalyst remnants at 0° C. Upon letting the filtrate stand at −78° C. overnight, further remnants of the catalyst are separated. The supernatant solution is fully evaporated under vacuum (0.2 torr), the residue is dried for several hours at 10³ torr, taken up in 120 ml of pentane, stirred for a short time and filtered. The white frit residue is washed with pentane and dried under 0.2 torr. One obtains 7.8 g of trans-1-lithium-1-butene, containing 9.48% Li. After the silylation of this product with trimethylchlorosilane, processing and distillation, as described in Example 1, this yields trans-1-trimethylsilyl-1-butene at 97% (according to GC analysis), which was identified by $^1$H-NMR-spectroscopy.

EXAMPLE 36

In a suspension of 0.58 g (1.28 mMoles) of 8 (see Examples 25 to 27) in 20 ml of THF, 1.81 liters (76 mMoles) of gaseous 1-butene are dissolved, which is followed by mixing the suspension at 0° C. under stirring with 0.92 g (0.13 Mole) of lithium sand. After stirring for 50 hours at 0° C. it is filtered and the lithium hydride is washed with THF. An aliquot of the solution (4.0 ml of a total of 43.6 ml) yields after evaporation of the THF and hydrolysis, 200 ml of gas (at 20° C., 1 bar) with a total of 30.0% butenes. On the basis of the amount of butene one calculates a yield of LiC$_4$H$_7$ of 40.7%. Upon mixing an aliquot of the solution with trimethylchlorosilane, as described in Example 1, one obtains a mixture of the isomeric silanes (H$_3$C)$_3$SiC$_4$H$_7$, which are, according to the $^1$H-NMR-spectrum or GC analysis, predominantly a mixture of cis-and trans-1-trimethylsilyl-2-butene.

EXAMPLE 37

In a suspension of 6.29 g (0.91 Mole) of lithium sand in 100 ml of THF are added at 0° C. and under stirring, in consecutive order, 33.8 g (0.48 Mole) of 1-pentene and 1.45 g (2.85 mMole) of complex 16 (Examples 28 to 33). The mixture is stirred for 5 days at 0° C., followed by filtration and washing of the solid (LiH) with THF. Of the total of 169 ml of filtrate, 2.50 ml contain, according to the acidimetric lithium determination, 4.30 g-atoms of Li, which corresponds to a yield in LiC$_5$H$_9$ of 64%.

In order to characterize the organolithium compound LiC$_5$H$_9$, 86.5 ml of the filtrate are mixed with excess trimethylchlorosilane, as described in Example 1. Processing or distillation yields, among others, 10.6 g of a fraction (B.P. 133° C./760 torr), which is trans-1-trimethylsilyl-1-pentene (18), according to the $^1$H-NMR-spectrum.

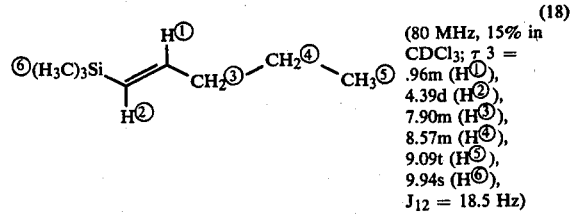

(18)
(80 MHz, 15% in CDCl$_3$; $\tau$ 3 = .96m (H①), 4.39d (H②), 7.90m (H③), 8.57m (H④), 9.09t (H⑤), 9.94s (H⑥), J$_{12}$ = 18.5 Hz)

In order to isolate the trans-1-lithio-1-pentene, 80 ml of the filtrate are concentrated under vacuum to 20 ml, are mixed with 80 ml of pentane and filtered. The filtrate is kept for 12 hours at −78° C., and is then syphoned off at −78° C. from the catalyst remnants that separated. The solution so obtained is completely evaporated under vacuum, the residue is dried at 20° C. and 10$^{-3}$ torr to constant weight, is taken up in 100 ml pentane, stirred for one-half hour and filtered. The white precipitate is washed with pentane and dried at 0.2 torr. One obtains 3.14 g of trans-1-lithio-1pentene in the form of white powder. LiC$_5$H$_9$ (MW=75.9); calc. 9.32% Li; fd. 9.29% Li.

EXAMPLE 38

In a manner analogous to Example 34, 21.6 g (0.20 Mole) of 1,7-octadiene are left to react in the presence of 1.25 g (2.76 mMoles) of complex 13 (Example 1) as catalyst, with 5.82 g (0.84 Mole) of lithium sand in 150 ml of THF for 11 days at 0° C. The suspension is filtered and lithium hydride is washed with THF. Of a total of 172 ml of the filtrate, 5.0 ml contain, according to the acidimetric determination, 6.94 g-atoms of lithium, corresponding to a total yield of organolithium compounds of 57%.

The organolithium compounds in solution are characterized in the form of their trimethysilyl derivatives. For that purpose, 77 ml (of a total of 172 ml) of the solution, are mixed with trimethylchlorosilane, as described in Example 1. The processing or distillation yields 7.67 g of a fraction with B.P. 55°–63° C./0.7 torr, as well as 1.55 g of a fraction of B.P.54°–55° C./10$^{-3}$ torr. According to the $^1$H-NMR-spectrum, the first fraction consists of trans-1-trimethylsilyl-1,7-octadiene (19), and the second fraction essentially of bis-1,8-(trans-trimethylsilyl)-1,7-octadiene (20), i.e.,

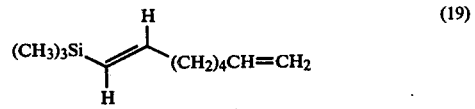

(19)

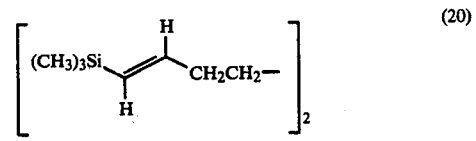

(20)

in the case of 1,7-octadiene, the lithiation also occurs with high selectivity in the trans-1 position.

EXAMPLE 39

In 150 ml of absolute THF there are suspended or dissolved consecutively 1.79 g (3.95 mMoles) of complex 13 (Example 1), as well as 13.0 g (0.19 Moles) of 1,4-pentadiene; immediately thereafter one adds to the suspension, at 0° C. under stirring, 11.1 g (1.60 Mole) of lithium sand. The reaction mixture is stirred for 74 hours at 0° C. After this time period, a 5.0-ml sample of the solution contains 9.42 mg atoms of lithium. The suspension is diluted with 50 ml of THF, filtered at 0° C. and the LiH is washed with THF. During the 48-hour standing of the solution at −78° C., the organolithium compound 14 crystalizes out in the form of brown-color, coarse crystal. The crystals are separated from the mother liquor at −78° C., are washed with a little THF cooled to −78° C. and dried for one-half hour at 0° C. and one-half hour at 20° C. under vacuum (0.2 torr). One obtains 11.1 g of product with a ratio of 9.61% lithium (calc. for C$_4$H$_5$Li$_3$(THF)$_2$ 9.0% Li). On the basis of the $^1$H-NMR or $^{13}$C-NMR-spectra in combination with spin-spin-decoupling experiments, as well as on the basis of the silylation (see below), the organolithium compound is assigned structure 14. In order to record the $^1$H-NMR-spectrum, the product, with 9.61% Li, is recrystalized twice from an 1:1 THF-tetramethylethylenediamine mixture (crystalization respectively at −78° C.). The $^1$H-NMR-spectrum of 14 (15% in d$_8$-THF; 270 MHz; 27° C.; d-THF as internal standard): δ=7.54 dd (H$^1$), 5.37 d (H$^3$), 4.79 d (H$^4$), 3.03 d (H$^5$), 2.95 d (H$^2$), 3.54 m and 1.68 m (THF), 2.21 s and 2.06 s (tetramethylenediamine); I$_{12}$=16.3 Hz, I$_{13}$=5.4 Hz, I$_{45}$=4.2 Hz.

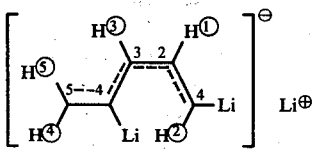

14

In order to record the 13C-NMR-spectrum, the raw product is recrystalized from THF (crystalization at −78° C.). The 13C-NMR-spectrum of 14 (100 MHz; 10% in d8-THF, at 25° C.): δ (ppm)=84.6 t (C5), 97.6 (wide) (C1), 100.4 d (C3), 153.9 d (C2), 187.7 (wide) (C4). The widening of the signals of the 13C1 and 13C4 nuclei indicates the presence of two Li-C bonds. In the reaction of 1.07 g of 14 with trimethylchlorosilane, as described in Example 1, one obtains, after processing or distillation, 0.85 g of a fraction of B.P. 45°–47° C./10−4 torr, which, according to the 1H-NMR-spectrum, is a mixture of the three stereoisomeric 1,4,5-tris (trimethylsilyl)-1,3-pentadienes (21) (65%), (22) (33%), and (23) (2%).

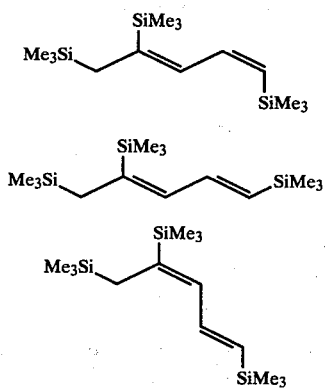

It was shown in a parallel experiment that in the reaction of pentadiene-1,4 with lithium, under the same conditions of reaction but in the absence of the catalyst, the formation of 14 occurs at best in trace quantities only.

EXAMPLE 40

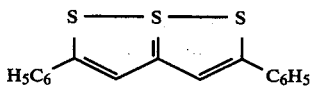

A solution of 0.34 g (1.1 mMoles) of 2,5-diphenyl-1,6,6a-trithiapentalene 24 and 0.30 g (2.2 mMoles) of ZnCl2 (anhydrous) in 50 ml of absolute THF, is saturated at 0° C. with ethylene (1 bar); immediately thereafter the preparation is mixed in an ethylene atmosphere at 0° C. and under stirring, with 1.45 g (0.21 Moles) of lithium sand. After a slight rise in temperature, ethylene absorption starts after 10–15 minutes, the rate of absorption being measured with the aid of a gas burette attached to the reaction vessel. During the ethylene absorption, the suspension is vigorously stirred and the temperature is kept at 0° C. Up to the end of the reaction, the reaction mixture absorbs within 6 hours 2.28 liters of ethylene (1 bar, 20° C.). The suspension is filtered to separate the lithium hydride, and the lithium hydride is washed with THF. Of the total of 81.0 ml of the filtrate, 50 ml yield after evaporation of the THF, upon hydrolysis, 126 ml of gas (at 20° C., 1 bar), which, according to MS analysis consists of 84.8 Mole% of ethylene. On the basis of the amount of ethylene obtained during hydrolysis, the vinyllithium yield is calculated according to Equ. 7 at 76% (referred to ethylene).

EXAMPLE 41

A solution of 1.61 g (5.2 mMoles) of 2,5-diphenyl-1,6,6a-trithiapentalene (24) and 1.21 g (8.9 mMoles) of ZnCl2 (anhydrous) in 100 ml of absolute THF is saturated at 0° C. with propene (1 bar); immediately thereafter the preparation is mixed in a propene atmosphere at 0° C. and under stirring with 5.47 g (0.79 Moles) of lithium sand. The further performance of the experiment followed Example 40 as described for ethylene. Up to the end of the reaction, the reaction mixture absorbed within 12 hours 7.9 liters of propene (at 20° C., 1 bar). The suspension was filtered and the lithium hydride washed with THF. Of the total of 167.0 ml of filtrate, 7.0 ml yielded upon hydrolysis 372 ml of gas (20° C., 1 bar), consisting of 88.8 Mole% of propene(-balance: THF, H2). From the amount of propene obtained upon hydrolysis, the yield of organolithium compounds LiC3H5 was calculated according to Equ. 8 at 99.7% (referred to propene). The mixing of 40 ml of the filtrate with trimethylchlorosilane, and the subsequent processing and distillation, as described in Example 1, yielded 11.9 g of the isomeric silanes (CH3)3SiC3H5, with the composition: trans-1-propenyltrimethylsilane, 80.0%; cis-1-propenyl-trimethylsilane, 0.4%; isopropenyltrimethylsilane, 15.0%; and allyltrimethylsilane, 4.6%. The isolation of the organolithium compounds LiC3H5 from the THF solution, as described in Example 1, yields a product that consists of 91.3% trans-propenyllithium.

EXAMPLE 42

To a solution of 25.1 g (0.22 Mole) of 1-octene and 1.23 g (4.0 mMoles) of 2,5-diphenyl-1,6,6a-trithiapentalene (24) in 100 ml of absolute THF, there are added consecutively at 0° C. and under stirring, 1.15 g (8.5 mMoles) of ZnCl2 (anhydrous) and, in small portions, 3.09 g (0.45 Moles) of lithium sand. The preparation was stirred for a total of 22 hours at 0° C. During this period, 2.5-ml samples were withdrawn from the solution, filtered, and the lithium content in the filtrates determined acidimetrically. After 3.5, 6, and 22 hours, the lithium content in the samples is 4.2, 4.6 and 5.4 mMoles, respectively, corresponding to a lithium conversion to lithium octenyl and lithiumhydride, according to Equ. 9, of 75, 83 and 97%. The preparation is filtered and the lithiumhydride is washed with THF. Of the total of 167.0 ml of the filtrate, 47.0 ml are mixed, as described in Example 1, with 11.0 g (0.10 Moles) of trimethylchlorosilane. The processing or distillation yields 6.13 g of a fraction of B.P. 35°–43° C./0.2 torr, which, according to GC analysis or GC-MS-coupling analysis and 1H-NMR-spectrum, consists of 96.6% of trans-1-trimethysilyl-1-octene (25). According to this result,

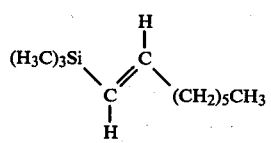

1-octene is lithiated according to the method described with a selectively greater than 96% in the trans-1 position.

Herein and in the claims, the catalyst is defined in the manner conventionally used in the art, i.e., in terms of its components, rather than attempting to speculate on the nature or structure of an active material which may be formed from these components.

What is claimed is:

1. A catalyst comprising (1) a complex of an alkali metal and, a polycyclic aromatic selected from the group consisting of anthracene, naphthalene and diphenyl or (2) a complex of the formula

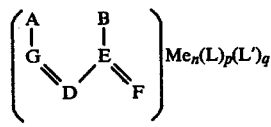

wherein
A and B are sulfur or oxygen;
G is a carbon atom bonded to a radical $R^1$;
D is a carbon atom bonded to a radical $R^2$ and there is a double bond between the carbon atom of G and D;
E is carbon;
F is oxygen, sulfur,

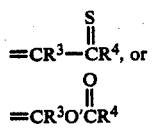

Me is an alkali metal;
n is an integer from 2 to 20;
L and L' are mono or poly-functional ethers or amines;
p and q are integers from 0 to 4;
$R^1$, $R^2$, $R^3$ and $R^4$ are independently hydrogen, alkyl, cycloalkyl, aralkyl or aryl groups;
with a metal halide, wherein the metal of said metal halide is a transition metal selected from the group consisting of $I_b$, $II_b$, $IV_b$, $V_b$, $VI_b$, $VII_b$ and VIII of the periodic system.

2. The catalyst according to claim 1, wherein the composition has the formula

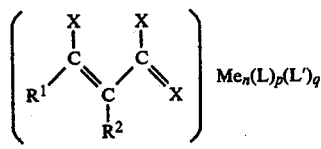

in which X is sulfur or oxygen.

3. The catalyst according to claim 2, wherein the composition has the formula

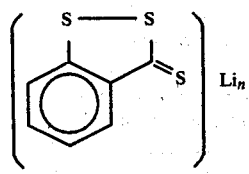

4. The catalyst according to claim 1, wherein the metal halide is cuprous chloride or ferric chloride.

5. The catalyst according to claim 1, wherein the composition has the formula

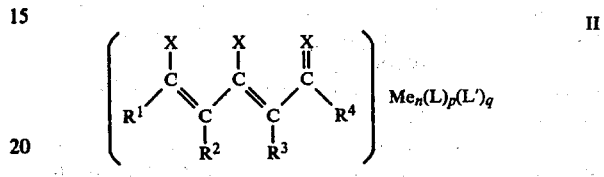

in which X is sulfur or oxygen.

6. The catalyst according to claim 5, wherein
X is sulfur,
$R^1=R^4$ is $C_6H_5$,
$R^2=R^3$ is hydrogen, and
Me is lithium.

7. The catalyst according to claim 6, wherein the metal halide is zinc chloride or palladium chloride.

8. The catalyst according to claim 5, wherein
X is sulfur,
$R^1=R^3$ is $C_6H_5$,
$R^2=R^4$ is hydrogen, and
Me is lithium.

9. The catalyst according to claim 8, wherein the metal halide is cupric chloride.

10. The catalyst according to claim 1, wherein the metal halide is of a metal selected from the group consisting of copper, gold, zinc, cadmium, titanium, zirconium, vanadium, niobium, tantalum, chromium, molybdenum, tungsten, manganese, iron, cobalt, nickel, ruthenium, rhodium, palladium, osmium, iridium, and platinum.

11. The catalyst according to claim 1, wherein the metal halide is of a metal selected from the group consisting of copper, iron, zinc, palladium, platinum, and rhodium.

12. The catalyst according to claim 1, wherein the metal halide is selected from the group consisting of zinc chloride, iron (III) chloride, copper (I) chloride, copper (II) chloride, molybdenum (VI) chloride, titanium (IV) chloride, chromium (III) chloride, molybdenum (V) chloride, manganese (II) chloride, cobalt (II) chloride, nickel (II) chloride, nickel (II) acetylacetonate, rhodium (III) chloride, platinum (II) chloride, and palladium (II) chloride.

13. The catalyst according to claim 1, wherein the metal halide is an anhydrous metal halide.

14. A catalyst composition comprising a complex of a polycyclic aromatic compound, an alkali metal, and a metal halide of a transition metal from group $I_b$, $II_b$, $IV_b$, $V_b$, $VI_b$, $VII_b$, and VIII of the periodic system.

15. The catalyst composition according to claim 14, wherein the polycyclic aromatic compound has from about 10 to 24 carbon atoms.

16. The catalyst composition according to claim 14, wherein the polycyclic aromatic compound is a member of the group consisting of naphthalene, anthracene, phenanthrene, and diphenyl.

17. The catalyst composition according to claim 14, wherein the alkali metal is lithium.

18. The catalyst composition according to claim 14, wherein the alkali metal is sodium or potassium.

19. The catalyst according to claim 14, wherein the metal halide is a metal selected from the group consisting of zinc chloride, iron (III) chloride, copper (I) chloride, copper (II) chloride, molybdenum (VI) chloride, titanium (III) chloride, titanium (IV) chloride, chromium (III) chloride, molybdenum (V) chloride, manganese (II) chloride, cobalt (II) chloride, nickel (II) chloride, nickel (II) acetylacetonate, rhodium (III) chloride, platinum (II) chloride, and palladium (II) chloride.

20. A catalyst according to claim 1, wherein two or more of $R^1$, $R^2$, $R^3$ and $R^4$ are closed into an aliphatic or aromatic ring system.

21. A catalyst composition comprising a complex of an alkali metal and at least one hetero compound of the formula

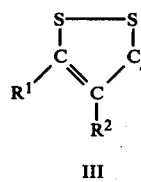 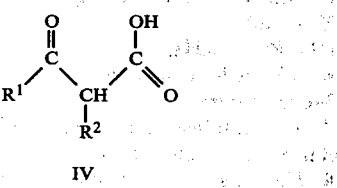

III IV

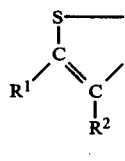 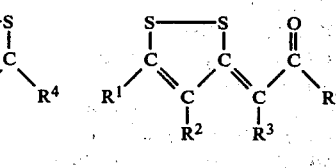

V VI

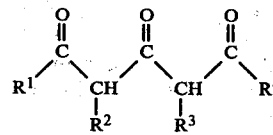

VII in which
X is sulfur or oxygen;
$R^1$, $R^2$, $R^3$ and $R^4$ represent hydrogen, alkyl of up to 20 carbon atoms, cycloalkyl, aralkyl, or aryl groups;
and at least one halide of a transition metal of Group $I_b$, $II_b$, $IV_b$, $V_b$, $VI_b$, $VII_b$ and VIII of the periodic system.

22. A catalyst according to claim 21, comprising a hetero compound of the formula

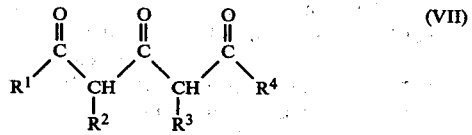

(VII)

wherein
$R^1$, $R^2$, $R^3$ and $R^4$ have the previously assigned significance.

23. A catalyst according to claim 21, comprising a metal halide of a transition metal of Group $I_b$.

24. A catalyst according to claim 21, comprising a metal halide of a transition metal of Group $II_b$.

25. A catalyst according to claim 21, comprising a metal halide of a transition metal of Group $IV_b$.

26. A catalyst according to claim 21, comprising a metal halide of a transition metal of Group $V_b$.

27. A catalyst according to claim 21, comprising a metal halide of a transition metal of Group $VI_b$.

28. A catalyst according to claim 21, comprising a metal halide of a transition metal of Group $VII_b$.

29. A catalyst according to claim 21, comprising a metal halide of a transition metal of Group VIII.

30. A catalyst according to claim 21, comprising a complex of a hetero compound of the formula

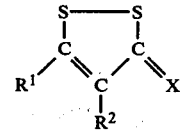

III wherein
X, $R^1$ and $R^2$ have the previously assigned significance.

31. A catalyst according to claim 21, comprising a complex of a hetero compound of the formula

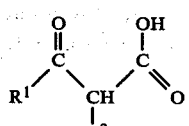

IV wherein
$R^1$ and $R^2$ have the previously assigned significance.

32. A catalyst according to claim 21, comprising a complex of a hetero compound of the formula

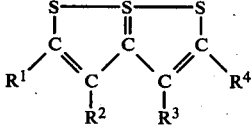

V wherein
$R^1$, $R^2$, $R^3$ and $R^4$ have the previously assigned significance.

33. A catalyst according to claim 21, comprising a complex of a hetero compound of the formula

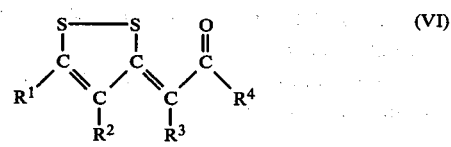

(VI)

wherein
$R^1$, $R^2$, $R^3$ and $R^4$ have the previously assigned significance.

34. A catalyst according to claim 21, wherein two or more of $R^1$, $R^2$, $R^3$ and $R^4$ are closed into an aliphatic or aromatic ring system.

35. A catalyst according to claim 34, wherein a polycyclic aromatic is formed, such aromatic selected from the group consisting of anthracene, naphthalene and diphenyl.

* * * * *